United States Patent [19]

Schmidt et al.

[11] Patent Number: 5,456,684
[45] Date of Patent: Oct. 10, 1995

[54] MULTIFUNCTIONAL MINIMALLY INVASIVE SURGICAL INSTRUMENT

[75] Inventors: Mark A. Schmidt, Hutchinson; James H. Dettmann, Duluth, both of Minn.

[73] Assignee: Hutchinson Technology Incorporated, Hutchinson, Minn.

[21] Appl. No.: 302,605

[22] Filed: Sep. 8, 1994

[51] Int. Cl.⁶ ................................................ A61B 17/00
[52] U.S. Cl. ........................... 606/41; 606/174; 606/46; 606/205; 606/207; 604/35
[58] Field of Search .................... 606/41, 45, 46, 606/48, 170, 174, 205–208, 142, 143; 604/35

[56] References Cited

U.S. PATENT DOCUMENTS 4,662,371  5/1987  Whipple et al. ................... 606/174 X
5,104,394  4/1992  Knoepfler ............................. 606/143
5,217,460  6/1993  Knoepfler ........................... 606/46 X
5,281,220  1/1994  Blake, III .............................. 606/46
5,354,291 10/1994  Bales et al. ......................... 606/46 X
5,360,428 11/1994  Hutchinson, Jr. .................. 606/46 X
5,374,277 12/1994  Hassler ............................... 606/170 X
5,391,166  2/1995  Eggers ................................ 606/170 X Primary Examiner—Peter A. Aschenbrenner
Attorney, Agent, or Firm—Faegre & Benson

[57] ABSTRACT

A multifunctional minimally invasive surgical instrument. The instrument includes a tool set on the opposite end of a support tube from a handle assembly. Grasping, manipulating, retracting, cutting, cauterizing, irrigation, suction, and electrosurgery functions can be performed by actuating the handle assembly. The tool set can also be rotated and articulated with respect to the handle assembly.

24 Claims, 16 Drawing Sheets

MULTIFUNCTIONAL MINIMALLY INVASIVE SURGICAL INSTRUMENT

BACKGROUND OF INVENTION

The present invention relates generally to surgical instruments. In particular, the present invention is a multifunctional minimally invasive surgical instrument.

Minimally invasive surgical procedures are being used with increasing regularity. These procedures are performed with minimally invasive surgical instruments which include a tool on the end of an elongated support tube opposite a handle. Access to the surgical site is provided by a trocar which is used to puncture and insert a cannula (hollow tube) through the patient's skin and muscle tissue. The tool of the surgical instrument is positioned at the surgical site after being inserted through the cannula. The surgeon then manipulates a lever or other actuator on the handle to perform the surgical operation. This procedure is carried out while viewing the surgical site on a video monitor. Minimally invasive surgical procedures of this type offer substantial benefits to the patient in terms of reduced post-operative pain, reduced recovery time, and lower cost.

The design and functionality of minimally invasive instruments can affect the outcome of surgical procedures. Currently available instruments typically have limited functionality. Examples of single function instruments include a grasping and manipulating instrument with jaws, a cutting instrument with a blade, and an irrigation/suction tube. Dual function instruments include those capable of coupling electricity through conductive jaws or blades to provide cauterization and electrosurgery functions in addition to grasping and cutting functions. Because of the limited functionality available with these instruments, surgical procedures requiring multiple functions are typically performed with instruments through several puncture sites, or by repeatedly withdrawing and inserting instruments having the required functionality.

Both of these alternative approaches have drawbacks. It is desirable to minimize the number of puncture sites to reduce the extent of post-operative pain and recovery time. Since the video camera used during these procedures produces only a two-dimensional view of the operative field, a high degree of skill is required to compensate for the lack of depth of field to prevent inadvertent trauma to tissue while inserting or withdrawing instruments. Changing instruments also takes time and distracts the surgeon. It is also expensive to keep the operating room adequately stocked with the range of instruments required by different surgeons for different surgical procedures.

It is evident that there is a continuing need for improved minimally invasive surgical instruments. A surgical instrument offering a high degree of functionality would be especially desirable since it would minimize the need for trocar puncture sites and repeated withdrawal and insertion of different instruments. The instrument should also be ergonomically designed so that it can be efficiently operated by a variety of surgeons.

SUMMARY OF INVENTION

The present invention is an improved multifunctional minimally invasive surgical instrument. One embodiment of the instrument includes a handle assembly with a support tube extending from a handgrip. First and second jaws are mounted to the distal end of the support tube for pivotal grasping cooperation with respect to one another. A jaw actuator is movably mounted to the handgrip and coupled to at least one of the jaws by a linkage extending through the support tube. By moving the jaw actuator, a surgeon can open and close the jaws.

The first jaw includes a blade-receiving structure. A blade is configured for movement between a retracted position within the distal end of the support tube, and a cutting position engaged with the blade-receiving structure of the first jaw. A blade actuator is movably mounted to the handgrip and coupled to the blade by a linkage which extends through the support tube. By moving the blade actuator, the surgeon can move the blade between its retracted and cutting positions. When the blade is extended to the cutting position, the surgeon can use the jaw actuator to move the blade in cutting cooperation with the second jaw.

Another embodiment of the instrument includes a suction/irrigation tip within the support tube. The tip is configured for movement between a retracted position between the jaws and handle assembly, and an extended position beyond the jaws. A suction/irrigation tip actuator is movably mounted to the handle assembly, and coupled to the suction/irrigation tip by a linkage extending through the support tube. The suction/irrigation tip is moved between the extended and retracted positions by the surgeon by actuating the suction/irrigation tip actuator. Suction and irrigation source tubes extend from the suction/irrigation tip through the support tube, and couple the tip to suction and irrigation fluid sources. Control members mounted on the handle assembly control suction and irrigation fluid flow through the source tubes to the tip.

Yet another embodiment of the instrument includes jaws with electrically conductive members. Electrical conductors extending from the electrically conductive members through the support tube couples electricity to the jaws so they can be used by a surgeon to perform electrosurgery and cauterization.

Still another embodiment of the surgical instrument includes a rotating mount for mounting the support tube to the handle assembly. A knob mounted to the support tube can be used by the surgeon to rotate the support tube, and therefore the jaws and blade, with respect to the handle assembly.

Another embodiment of the instrument includes an articulating joint for articulating the distal end of the support tube. An articulation actuator in the handle assembly is movably mounted with respect to the handgrip and coupled to the distal end of the support tube by a linkage. By using the articulation actuator the surgeon can articulate the distal end of the support tube.

DETAILED DESCRIPTION OF THE PREFERRED EMBODIMENTS

Figure 1:
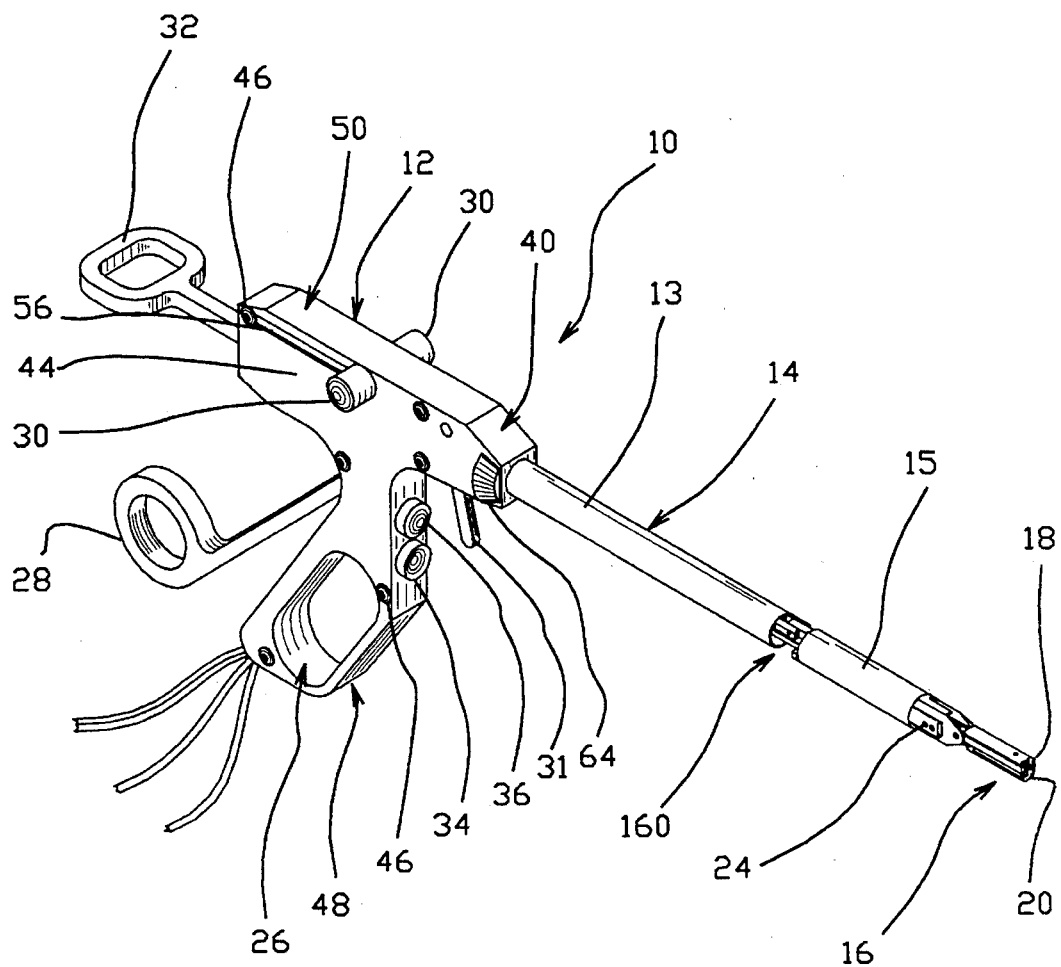
FIG. 1 is a perspective view of a multifunctional minimally invasive surgical instrument in accordance with the present invention.
Figure 2:
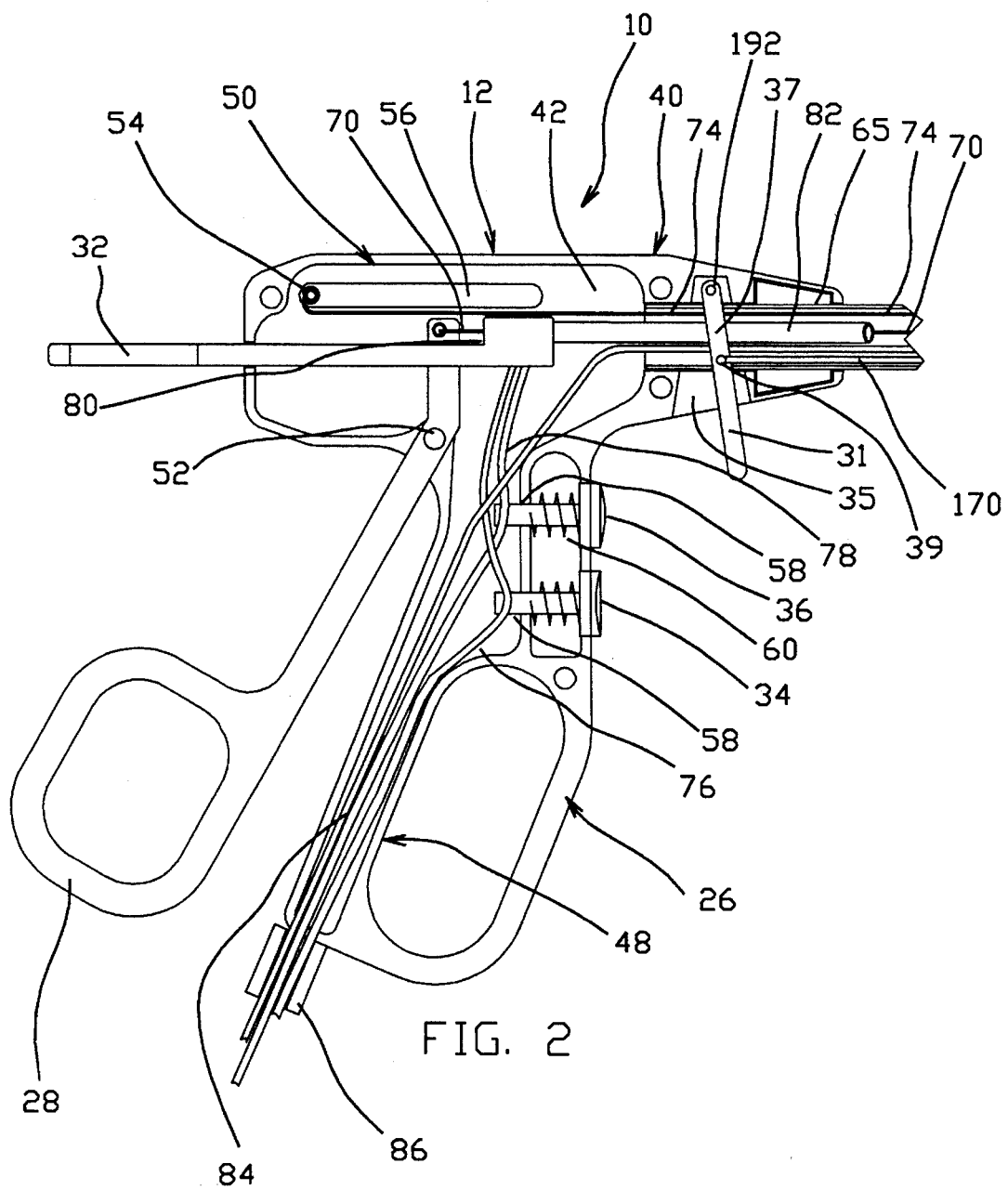
FIG. 2 is a sectional view of the handle assembly of the instrument taken from the side shown on FIG. 1.

A multifunctional minimally invasive surgical instrument 10 in accordance with the present invention is illustrated generally in FIGS. 1 and 2. As shown, surgical instrument 10 includes a handle assembly 12, support tube 14 and tool assembly 16. Tool assembly 16 is mounted to a distal end 15 of the support tube 14 and includes jaws 18 and 20, cutting blade 22 (not visible in FIGS. 1 or 2) and suction/irrigation tip 24, all of which are capable of being positioned within the outer diameter of the support tube. Handle assembly 12 includes handgrip 26, a jaw actuator such as trigger 28, a blade actuator such as knobs 30, an articulation actuator such as trigger 31, a suction/irrigation tip actuator such as switch 32, suction control button 34, irrigation control button 36 and tool assembly rotation actuator such as knob 64. Support tube 14 and tool assembly 16 are inserted into the body of the patient through a cannula (not shown) in a conventional manner. Instrument 10 can then be conveniently manipulated by a surgeon to perform a wide range of surgical functions without withdrawing the instrument from the patient's body.

Figure 3:
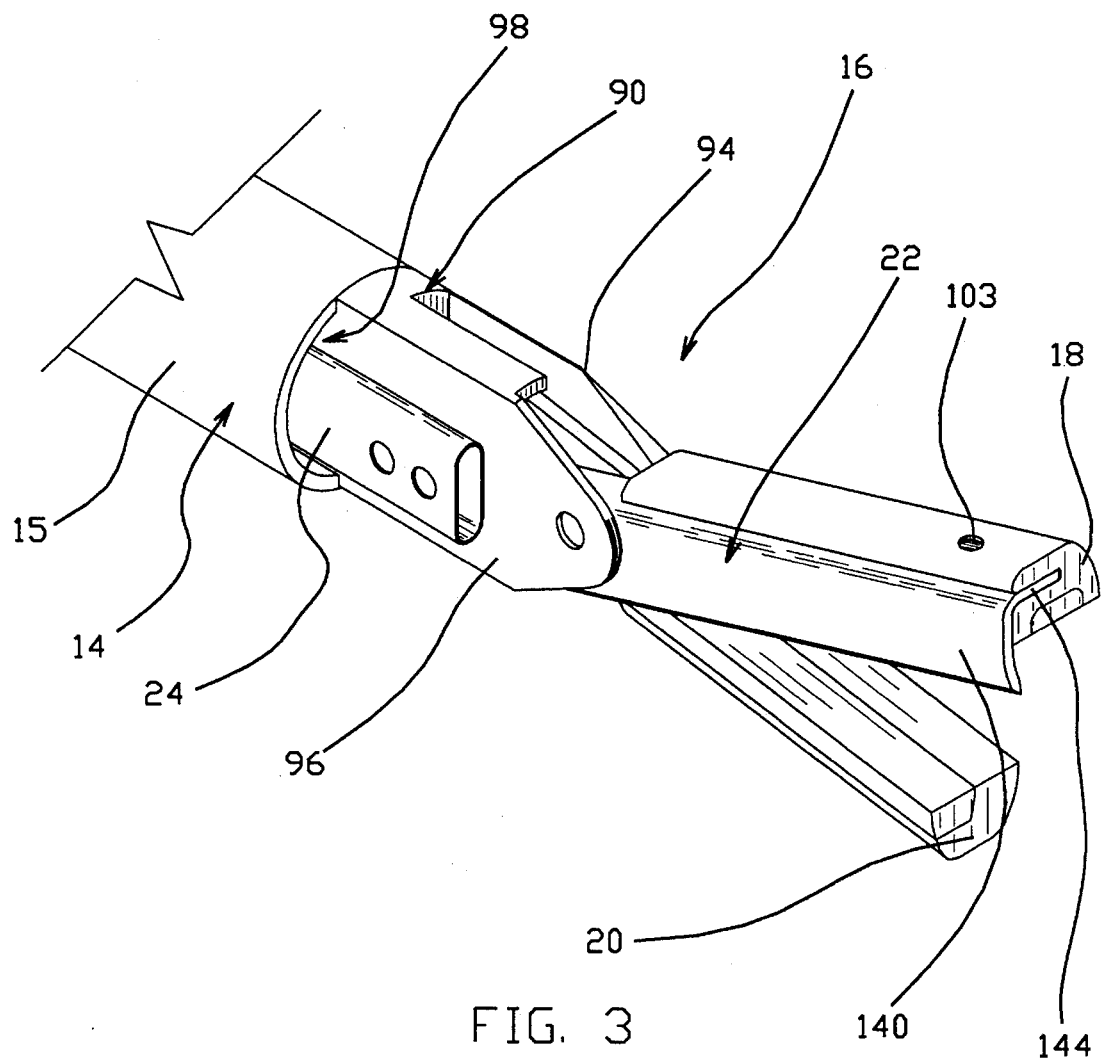
FIG. 3 is a detailed view of the distal end of the instrument shown in FIG. 1, illustrating the jaws, blade, and suction/irrigation tip.

Trigger 28 is actuated by the surgeon's thumb to open and close jaws 18 and 20 with respect to one another and perform grasping, manipulating and retracting functions. As will be described in greater detail below, when jaws 18 and 20 are closed, knob 30 can be actuated to slide blade 22 from a retracted position within support tube 14 to an extended or cutting position on jaw 18 (as shown in FIG. 3). When blade 22 is in the cutting position, trigger 28 can be actuated in a manner causing the blade to move in scissor-like cutting cooperation with jaw 20 to perform a cutting function. Blade 22 is withdrawn to its retracted position by sliding knobs 30 rearwardly when jaws 18 and 20 are closed. Suction and irrigation functions are initiated by actuating switch 32 to extend tip 24 from the retracted position shown in FIG. 1 to an extended position beyond jaws 18 and 20. Suction button 34 is actuated by the surgeon to couple tip 24 to a vacuum source (not shown) and thereby provide a suction function. In a similar manner, irrigation button 36 is actuated to connect tip 24 with a source of pressurized irrigation fluid (not shown) to provide an irrigation function. As described in greater detail below, jaws 18 and 20 include metal or other electrically conductive material portions, and are connected to monopolar and/or bipolar sources of electricity (not shown) through switches (also not shown). By actuating the switches, the surgeon can use jaws 18 and 20 to perform cauterization and electrosurgery functions. Blade 22 can be retracted during the performance of cauterization and electrosurgery functions. Tool assembly 16 can also be rotated and articulated with respect to handle assembly 12 to move the tool set within the surgical site without moving the handle assembly. Knob 64 is actuated to rotate support tube 14 and the tool assembly 16 thereon. The distal end 15 of support tube 14, and tool assembly 16, are articulated about joint 160 by actuating trigger 31.

Handgrip 26 is two-piece polymer member including a base 40 with a cavity 42, and a cover plate 44 secured to the base by fasteners 46 to enclose the cavity and other components of handle assembly 12 mounted therein. Base 40 includes a finger-engaging section 48 positioned below a tube mounting section 50. Trigger 28 is pivotally mounted to mounting section 50 by pin 52. A jaw linkage including actuator bar 68 (FIGS. 8 and 9) and spring steel rod 70, which are slidably mounted within support tube 14, operatively couples trigger 28 to jaws 18 and 20. The thumb-engaging section of trigger 28 extends from pin 52 to a position behind finger-engaging section 48, so it can be conveniently actuated by the thumb of the surgeon grasping handgrip 26 to open and close jaws 18 and 20.

Switch 32 is mounted to base 40 for slidable motion along an axis generally parallel to support tube 14, and includes a thumb-engaging section which extends rearwardly from mounting section 50 of handgrip 26. A suction/irrigation tip linkage including manifold 80 and tube 82 operatively connects switch 32 to tip 24. In one embodiment, tube 82 is metal, but includes a flexible polymer section extending across joint 160. The flexible section of tube 82 should have sufficient stiffness in the axial direction that tip 24 can be extended and retracted through activation of switch 32, even when instrument 10 is articulated at joint 160. The surgeon can thereby actuate switch 32 to extend and retract suction/irrigation tip 24 using the thumb of the hand grasping handgrip 26.

Figure 12:
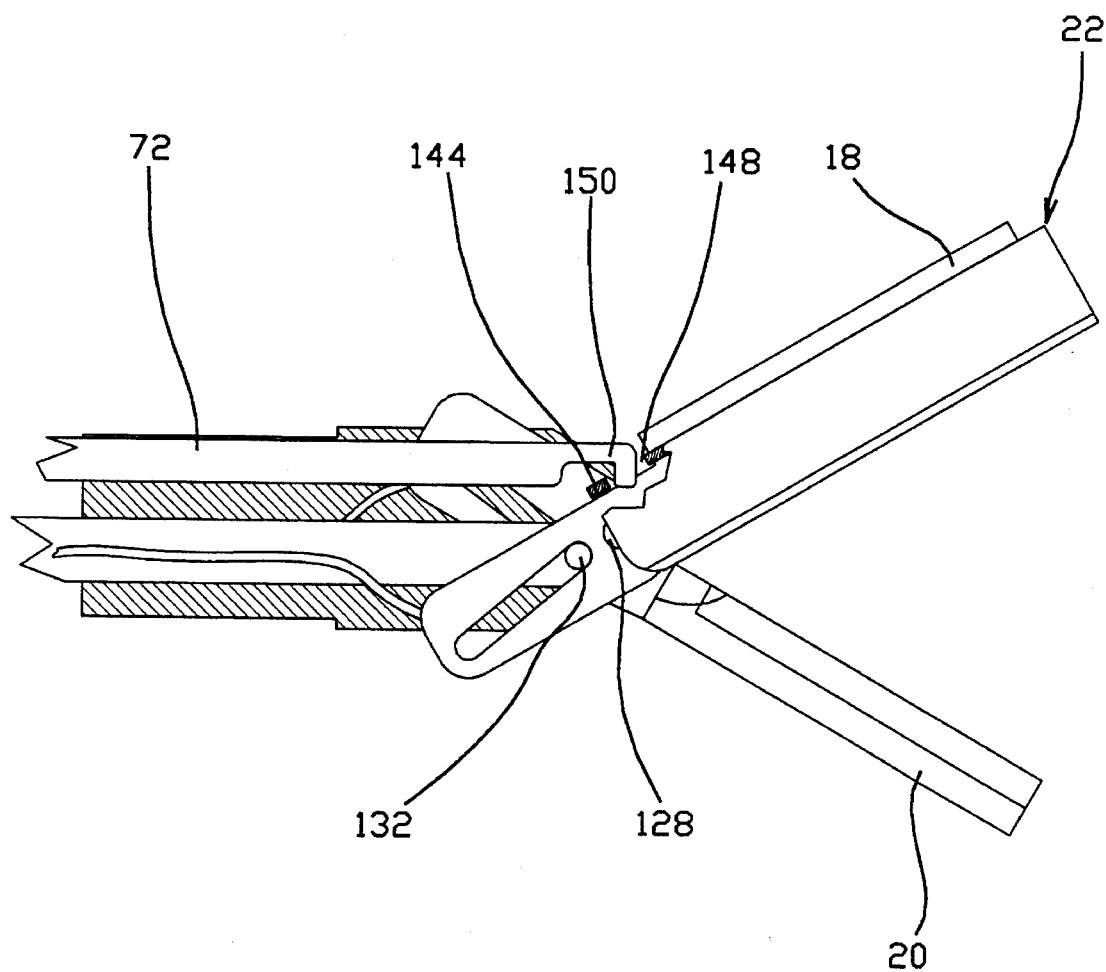
FIG. 12 is a detailed sectional view of the distal end of the instrument, with the blade in its cutting position and the jaws open.
Figure 13:
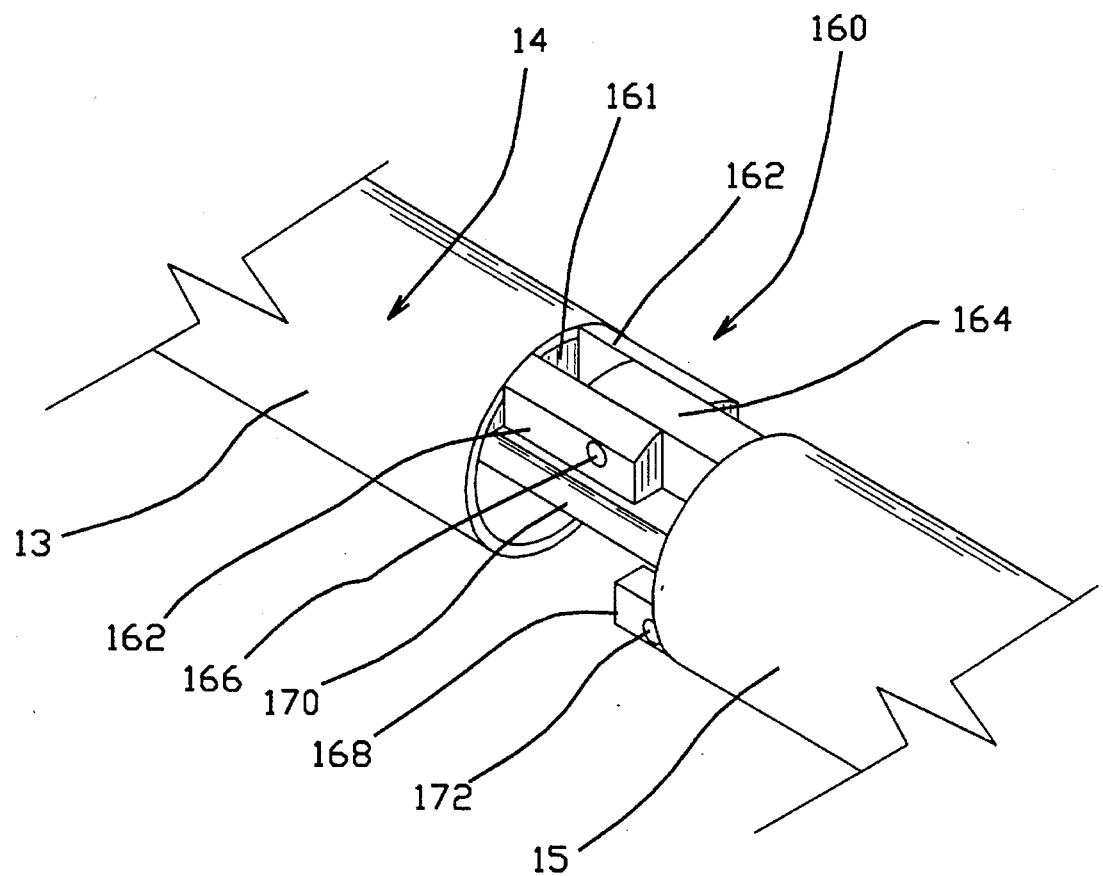
FIG. 13 is detailed view of the articulation joint in the support tube of the instrument shown in FIG. 1.
Figure 14:
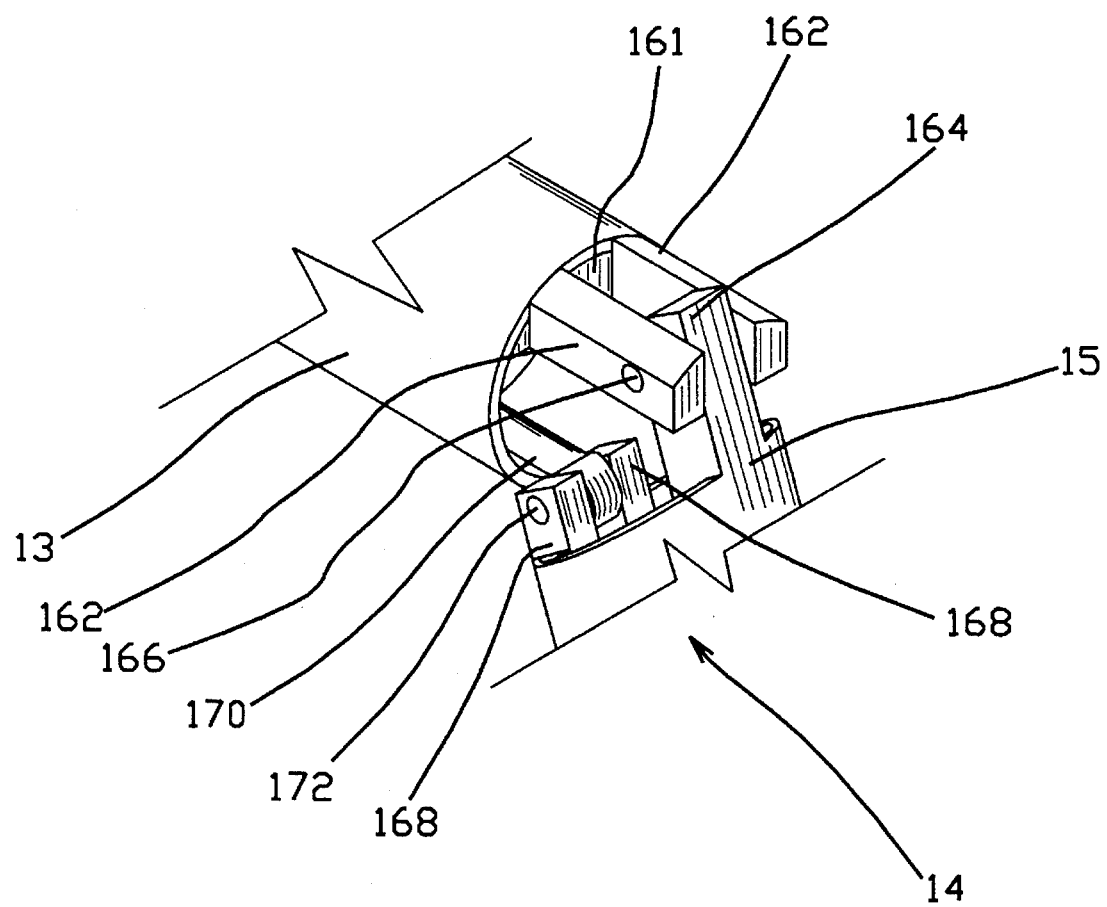
FIG. 14 is a view of the articulation joint shown in FIG. 13, in the articulated position.

Knobs 30 are mounted to a shaft 54 which extends through elongated slots 56 in the opposite sides of mounting section 50 of handgrip 26. Shaft 54 is operatively connected to blade 22 by a blade linkage including actuator bar 72 (FIGS. 9 and 12) and stainless spring steel rod 74 which are slidably mounted within and extend through support tube 14. Knobs 30 can thereby be used by the surgeon to slide blade 22 between the retracted and cutting positions.

Suction button 34 and irrigation button 36 are mounted to the forward edge of handgrip 26 at a location between finger-engaging section 48 and tube mounting section 50. Buttons 34 and 36 each cooperate with a pinch valve 58 slidably mounted within base 40 and biased toward the buttons by springs 60. Conventional suction and irrigation sources (not shown) are fluidly connected to suction/irrigation tip 24 through a flexible suction tube 76 and irrigation tube 78, respectively, that extend through handgrip 26 and converge in manifold 80. Tubes 76 and 78 are releasably pinched by pinch valves 58, and are opened by actuating suction button 34 and irrigation button 36, respectively. Manifold 80 is connected to a proximal end of suction/irrigation tip 24 by tube 82 extending through support tube 14. Suction button 34 and irrigation button 36 can be easily actuated by the surgeon's forefinger to initiate suction and irrigation functions, respectively.

Electrical connection to jaws 18 and 20 is provided through flexible wires 84 which extend through handgrip 26 and support tube 14. Wires 84, as well as suction tube 76 and irrigation tube 78, extend from the bottom of handgrip 26 through a strain relief clamp 86.

Support tube 14 is rigid polymer or stainless steel tube having a proximal end 13 rotatably mounted to the forward end of mounting section 50 of base 40. In one embodiment, support tube 14 is a stainless steel member sized to fit through a ten millimeter cannula. Knob 64 is mounted to the proximal end 13 of support tube 14 within recess 65 in handgrip 26, and extends from the opposite sides of the handgrip. The surgeon can rotate support tube 14, and therefore the orientation of tool assembly 16 at the surgical site, by actuating and turning knob 64. Rods 70 and 74, tube 82 and wires 84 are sufficiently flexible to accommodate the rotation of support tube 14.

As shown in FIGS. 1 and 13–16, the distal end 15 of support tube 14, and the tool assembly 16 mounted thereon, can be articulated with respect to the distal end 13 of the tube at joint 160. Joint 160 includes a pair of legs 162 extending from proximal section 13 of tube 14, and a leg 164 mounted to and extending from distal section 15. Legs 162 extend from a guide insert 161 mounted within section 13 of tube 14, and are pivotally mounted to leg 164 by pivot pin 166. Distal section 15 of tube 14 includes a guide insert 163 having a pair of spaced legs 168 at a diametrically opposed position to leg 164. Stainless spring steel actuator rod 170 extends through proximal section 13 of tube 14 and is pivotally mounted between legs 168 by pivot pin 172.

Figure 21:
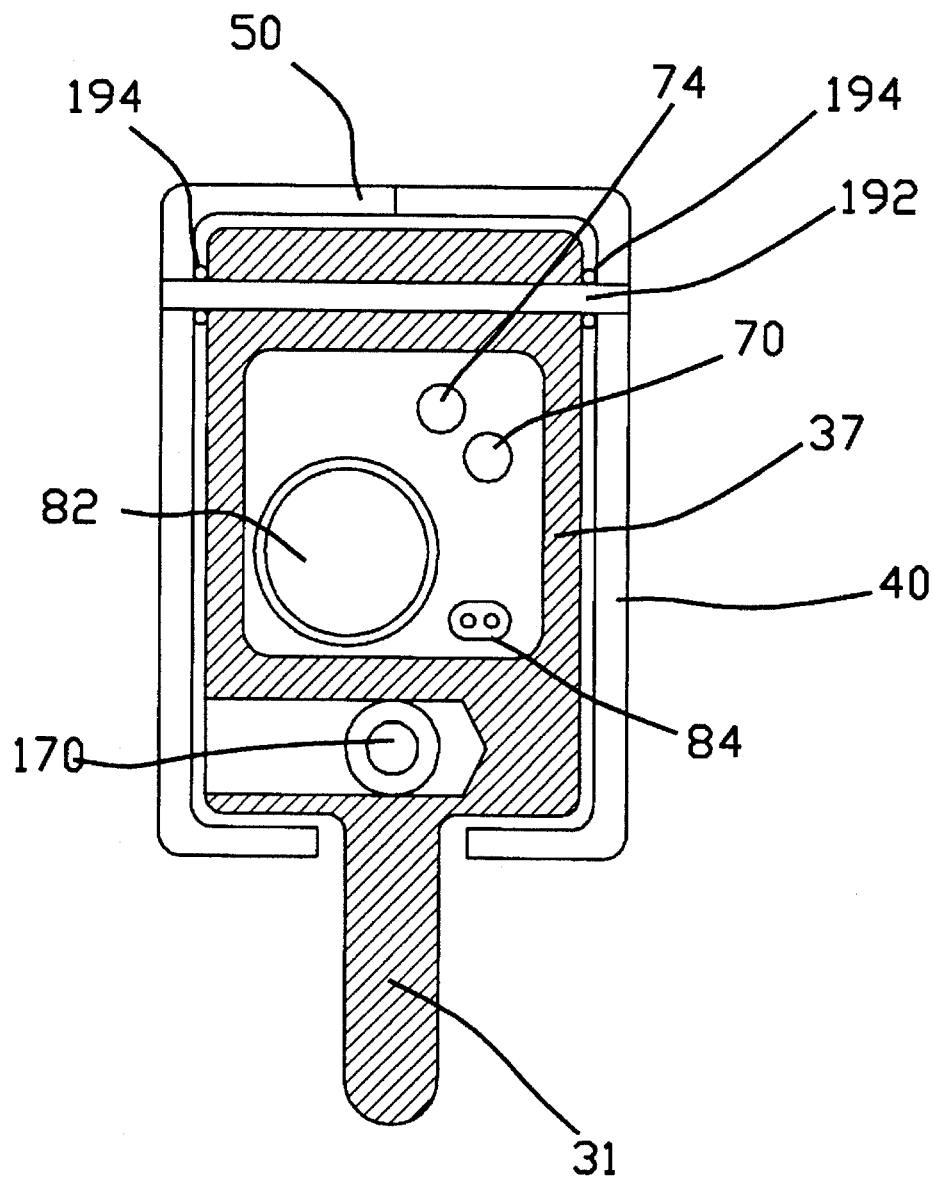
FIG. 21 is a detailed sectional view of the handle assembly of the instrument, illustrating the articulation trigger.

As shown in FIGS. 2 and 21, articulation trigger 31 is pivotally mounted by pin 192 within recess 35 of handgrip 26. O-rings 194 are positioned around pin 192 between both sides of trigger 31 and the outer walls of tube mounting section 50 of handgrip 26. Trigger 31 extends from the bottom of tube mounting section 50 of handgrip 26, in front of finger-engaging section 48. A ring-shaped section 37 of trigger 31 has an opening through which rods 70 and 74, tube 82 and wires 84 extend. The proximal end of actuator rod 170 is pivotally connected to trigger 31 below ring-shaped section 37 by pin 39. By moving actuator rod 170 in a generally longitudinal forward and reverse direction through actuation of trigger 31, an operator can articulate or pivot the distal section 15 of tube 14 and the tool assembly 16 thereon. Rods 70 and 74, the section of tube 82 at joint 160 and wires 84 are flexible, and will bend at joint 160 when trigger 31 is actuated to articulate tool assembly 16. Since rods 70 and 74, tube 82 and wires 84 are resilient, they will generate forces tending to resist the articulation when bent at joint 160. To counter these forces and provide friction that will retain trigger 31 and tool assembly 16 in the articulated position set by the operator, O-rings 194 are compressed between the trigger and the walls of handgrip 26.

Figure 15:
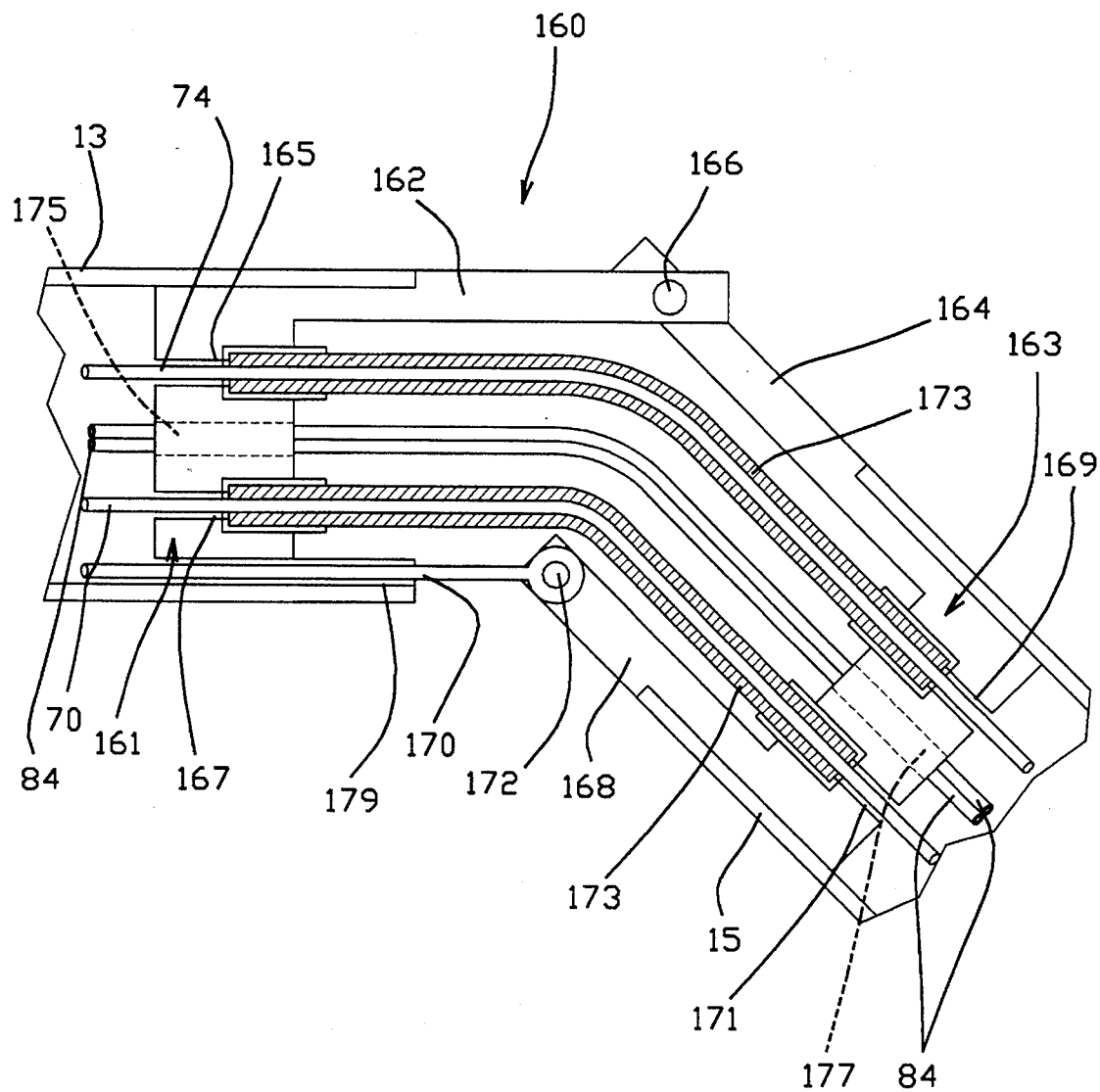
FIG. 15 is a detailed sectional view of the articulation joint shown in FIG. 13, in the articulated position.
Figure 16:
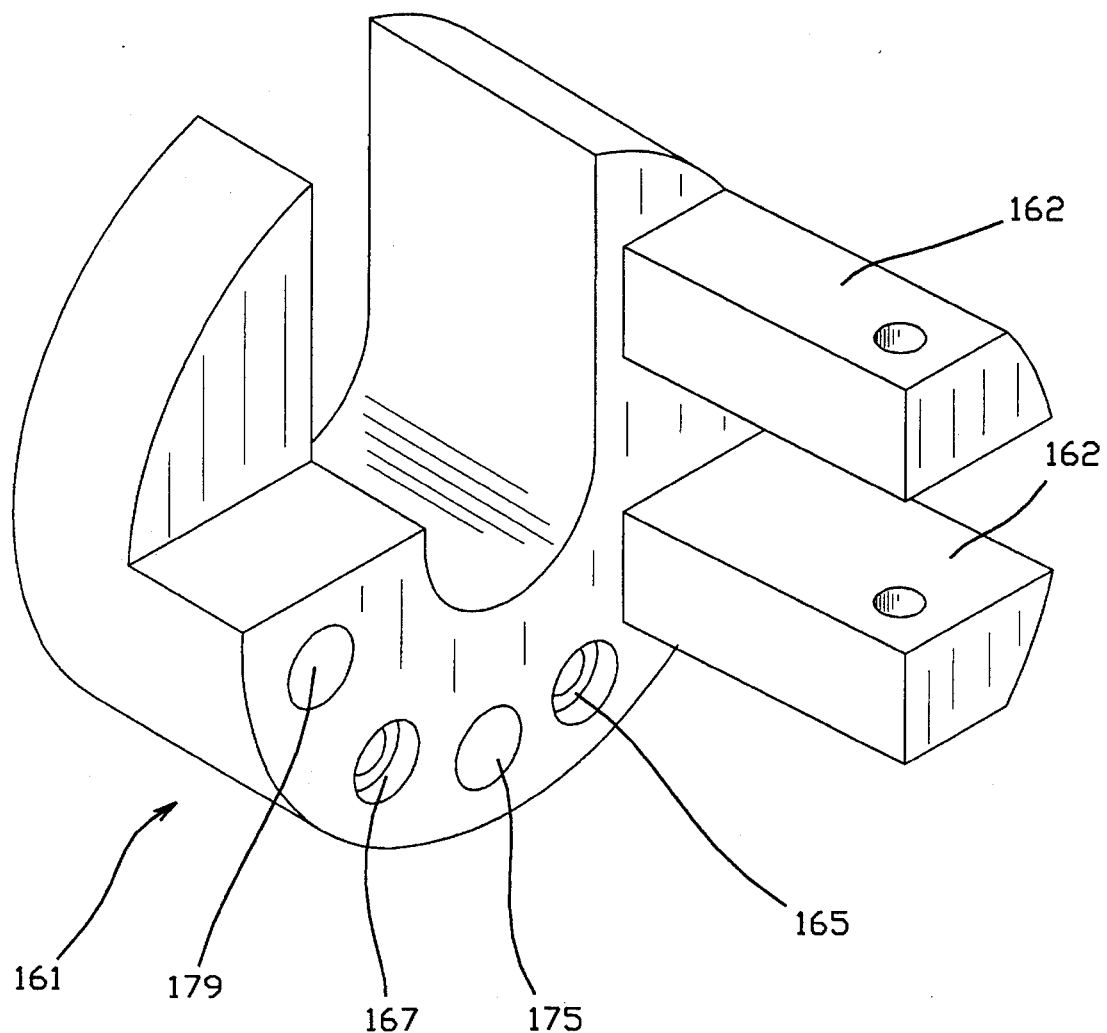
FIG. 16 is a detailed perspective view of the articulation guide insert shown in FIG. 15.

As shown in FIGS. 15 and 16, guide inserts 161 and 163 include apertures 165, 167 and 169, 171, respectively, through which rods 74 and 70 extend. Flexible tubes 173 surround rods 70 and 74 between guide inserts 161 and 163, and have their opposite end secured to the guide inserts within recesses in apertures 165, 167, 169 and 171. Wires 84 extend through apertures 175 and 177 in guide inserts 161 and 163, respectively. Rod 170 extends into joint 160 through aperture 179 in guide insert 161.

Tool assembly 16 can be described in greater detail with reference to FIGS. 3–7. As shown, jaws 18 and 20, blade 22 and suction/irrigation tip 24 are positioned and guided during actuation by jaw holder 90. Jaw holder 90 is shaped generally as a cylindrical section. Proximal end 92 of jaw holder 90 is sized to fit within the distal end 15 of support tube 14, while the distal end 94 extends beyond the support tube. Planar wall 96 extends between proximal end 92 and distal end 94 of jaw holder 90, and forms a cavity 98 in the distal end 15 of support tube 14. Cavity 98 houses suction/irrigation tip 24, and guides the tip as it is driven between its extended and retracted positions in response to actuation of switch 32.

Upper jaw 18 includes a grasping member 100 and a lever arm 102 extending from opposite sides of pivot aperture 104. An elongated slot 105 through lever arm 102 extends in a downwardly sloping direction from pivot aperture 104. Similarly, lower jaw 20 includes a grasping member 106 and a lever arm 108 extending from opposite sides of a pivot aperture 110. Slot 111 through lever arm 108 extends in an upwardly sloping direction from a position below pivot aperture 110.

Figure 4:
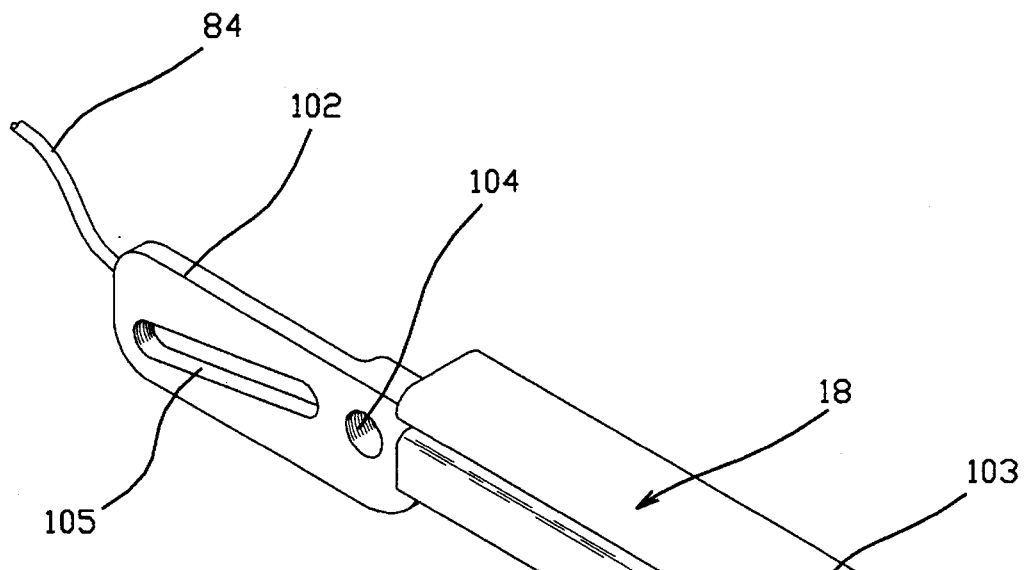
FIG. 4 is a detailed perspective view of the upper jaw shown in FIG. 3.
Figure 5:
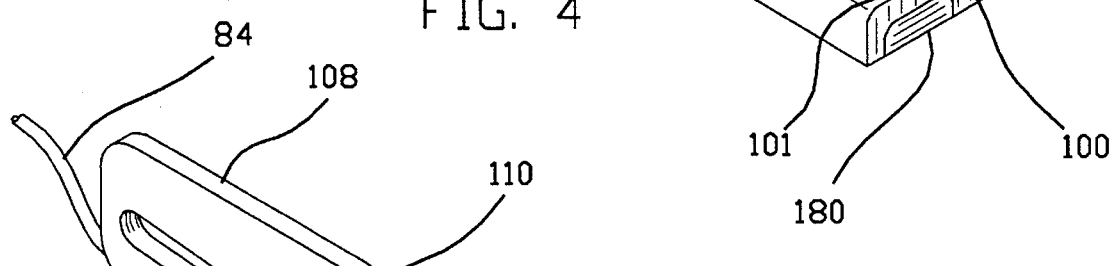
FIG. 5 is a detailed perspective view of the lower jaw shown in FIG. 3.
Figure 17:
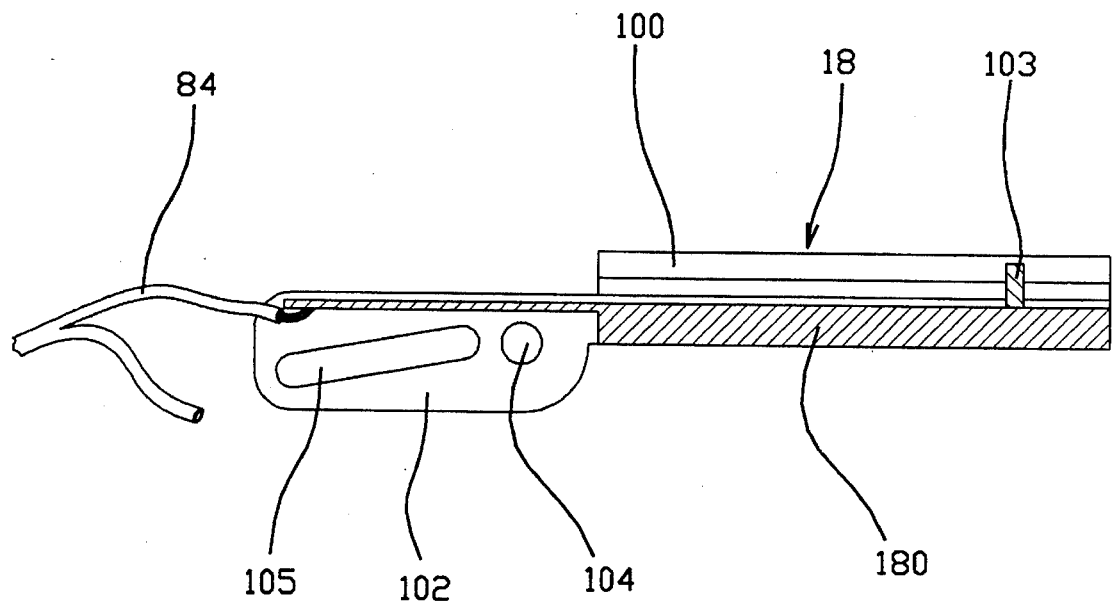
FIG. 17 is a sectional side view of the upper jaw shown in FIG. 4.
Figure 18:
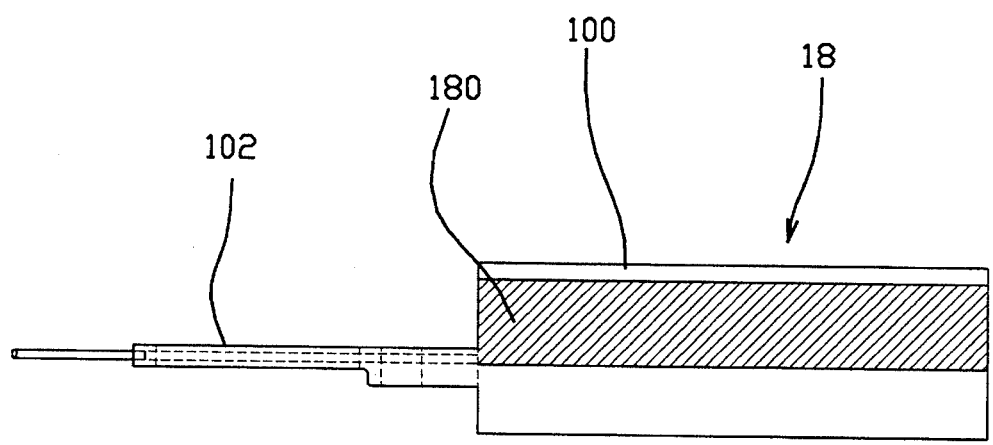
FIG. 18 is a top view of the upper jaw shown in FIG. 17.
Figure 19:
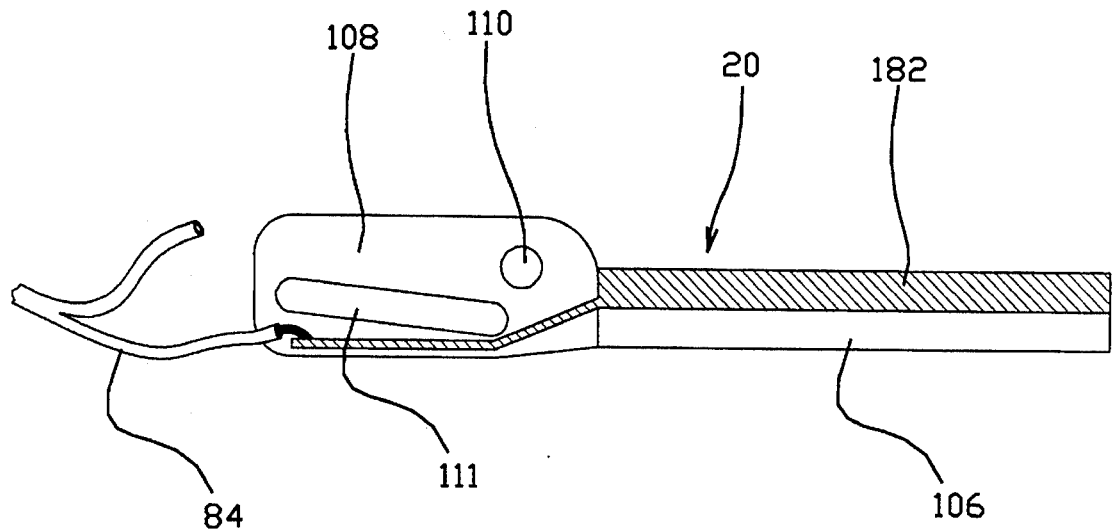
FIG. 19 is a sectional side view of the lower jaw shown in FIG. 5.
Figure 20:
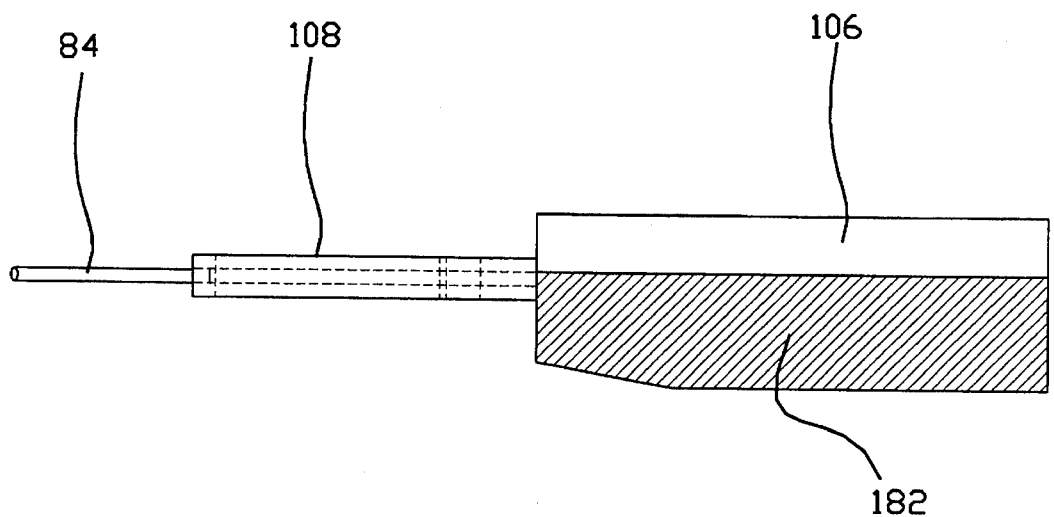
FIG. 20 is a top view of the lower jaw shown in FIG. 19.

As shown in FIGS. 4, 17 and 18, upper jaw 18 includes a metal or other conductive insert 180 surrounded by polymer, ceramic or other insulating material. Only the grasping surface and distal end of insert 180 is exposed. Similarly, and as shown in FIGS. 5, 19 and 20 lower jaw 20 includes a conductive insert 182 surrounded by insulating material, with the grasping surface, distal end and one side of the insert exposed. Wires 84 are connected to conductive inserts 180 and 182 at lever arms 102 and 108, respectively. The insulating material of jaws 18 and 20 must be thick enough and have appropriate dielectric properties to insulate conductive inserts 180 and 182 from one another. Conductive inserts 180 and 182 can thereby function as electrodes for cauterization and electrosurgery functions.

Jaws 18 and 20 can be manufactured by molding or otherwise forming the insulating material around conductive inserts 180 and 182. Electrical connection between conductive inserts 180 and 182 and wires 84 can be made before forming the insulating material around the conductive inserts to electrically isolate the connections. For example, jaws 18 and 20 can be molded in a two-cavity mold (not shown), with the ends of wires 84 separated by a short distance and extending into the cavities, with the inserts 180 and 182 attached to the wires (e.g., by soldering) and positioned in cavities. Keeper pin 103 of upper jaw 18 (described in greater detail below) can also be molded during the fabrication of jaw 18 by using a mold (not shown) with inserts that close around the pin so the insulating material will not occupy the space behind the pin.

Figure 6:
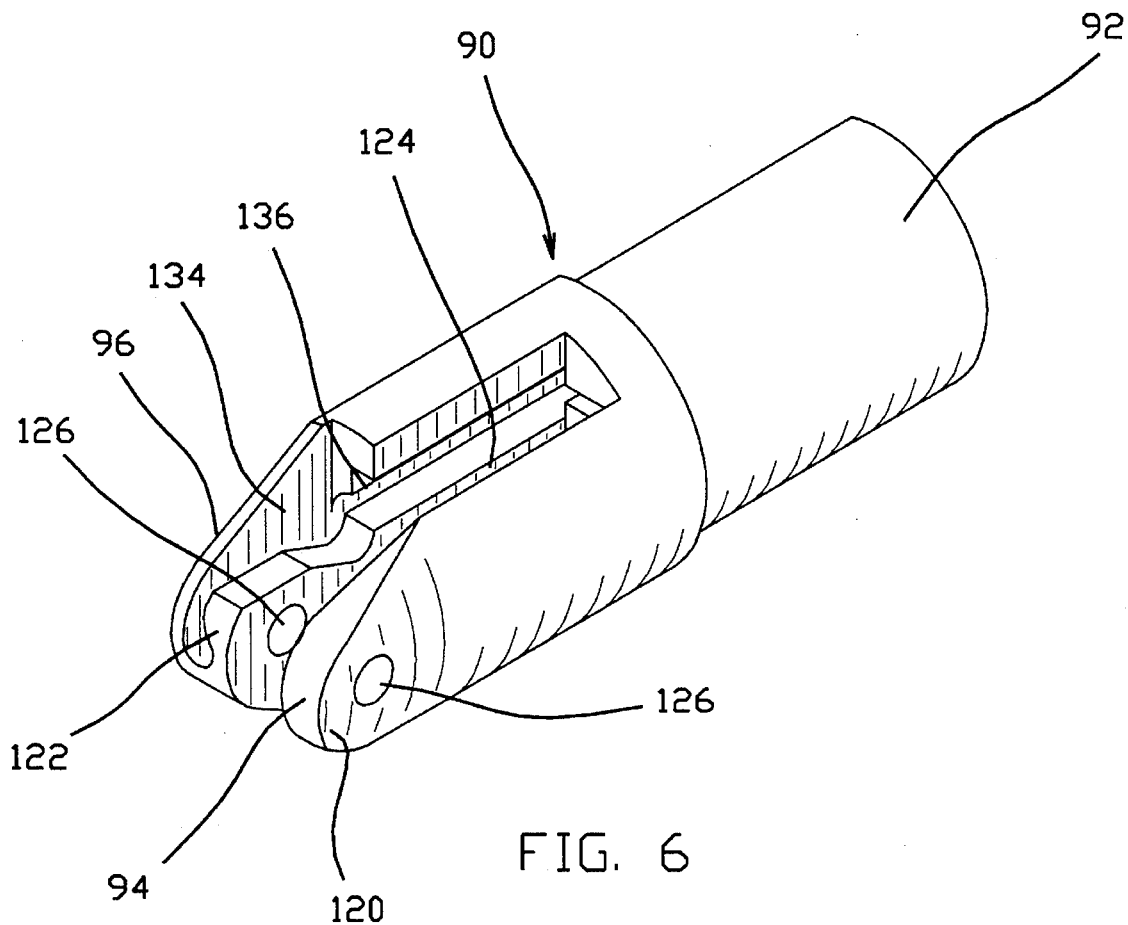
FIG. 6 is a detailed perspective view of the jaw holder shown in FIG. 3.
Figure 7:
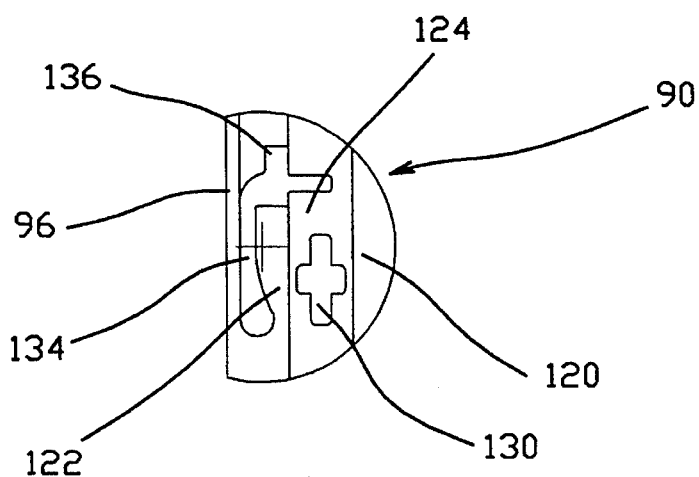
FIG. 7 is an end view of the jaw holder shown in FIG. 6, without the blade or jaws mounted thereto.

As shown in FIG. 6 and 7, jaw holder 90 includes at its distal end 94 a pair of jaw mounts 120 and 122 which are transversely spaced by gap 124. Apertures 126 extend through jaw mounts 120 and 122, and are sized to receive a pivot pin 128 (FIG. 8) which extends through apertures 104 and 110 to pivotally mount jaws 18 and 20 to jaw holder 90 with lever arms 102 and 108 positioned within gap 124.

Figure 8:
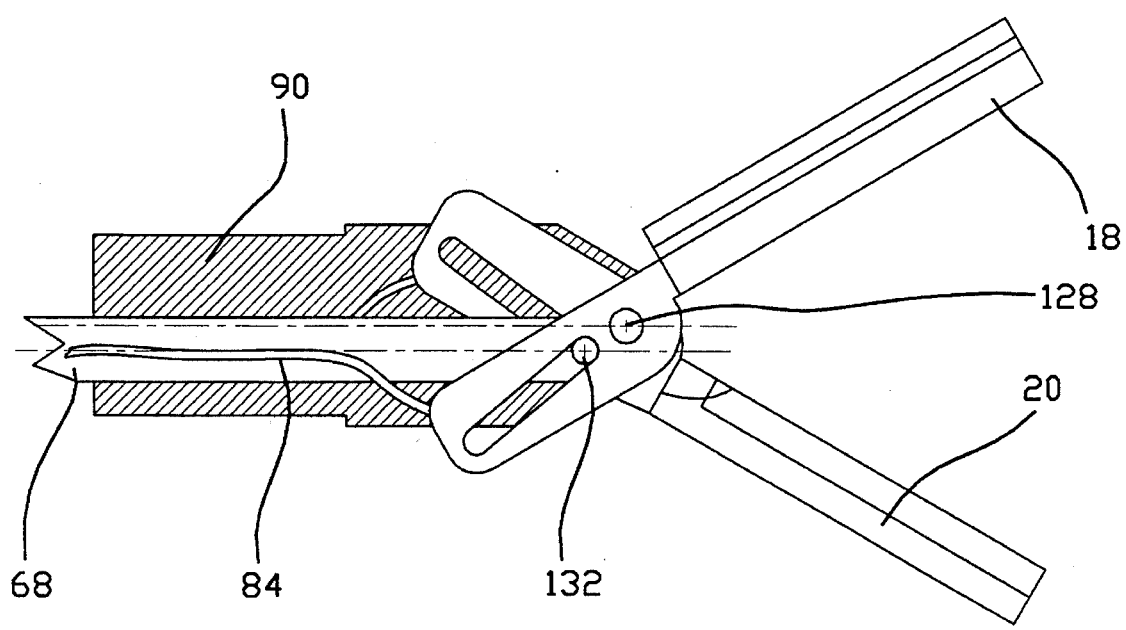
FIG. 8 is a detailed sectional view of the distal end of the instrument, illustrating the jaws in the open position.
Figure 9:
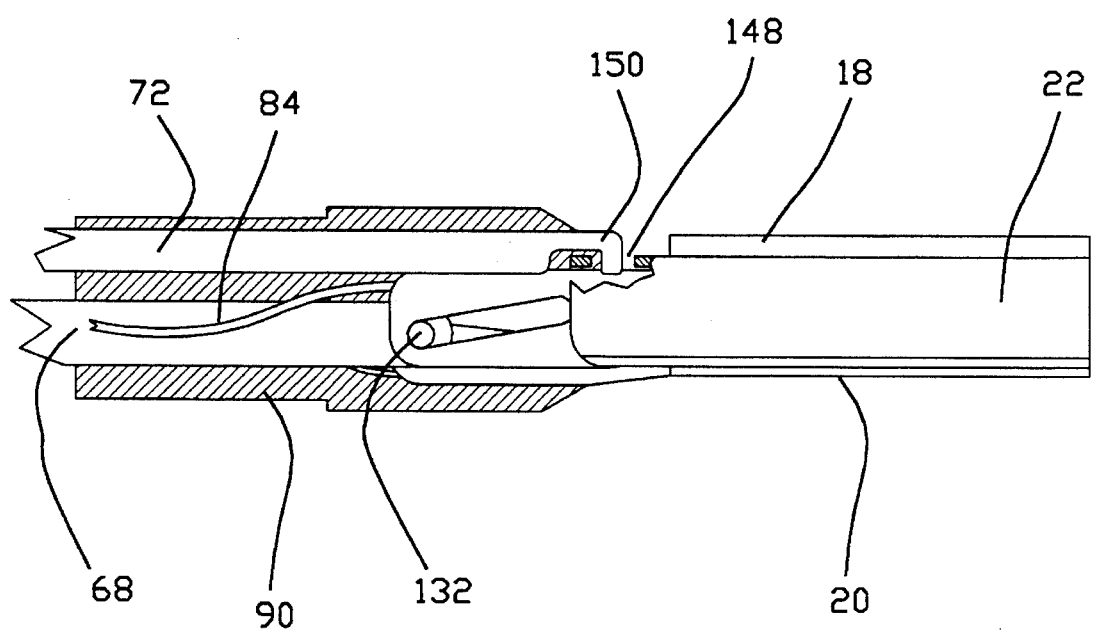
FIG. 9 is a detailed sectional view of the distal end of the instrument, illustrating the blade in the cutting position and the jaws in the closed position.

Guide slot 130 extends longitudinally through jaw holder 90 into communication with gap 124, and as shown in FIG. 8, is sized to slidably receive jaw actuator bar 68. Actuator pin 132 extends transversely from actuator bar 68 within gap 124 into slots 105 and 111 of jaws 18 and 20, respectively. When jaw actuator bar 68 is moved longitudinally toward jaws 18 and 20 in response to actuation of trigger 28 as shown in FIG. 8, the movement of pin 132 in slots 105 and 111 causes the jaws to pivot about pin 128 and open. In a complimentary manner, movement of jaw actuator bar 68 in a longitudinal direction toward handle assembly 12 causes pins 132 to close jaws 18 and 20 as illustrated in FIG. 9. As shown in FIG. 8, the axis along which pin 132 moves in response to actuation of trigger 28 is below pivot pin 128.

Jaw holder 90 also includes blade guide slot 134 and blade actuator slot 136. As shown in FIG. 7, blade guide slot 134 has an inverted "L" shaped cross-section and is sized to slidably receive blade 22. Blade guide slot 134 extends longitudinally through jaw holder 90. Actuator slot 136 extends longitudinally through jaw holder 90 and communicates with the upper leg of guide slot 134.

Figure 10:
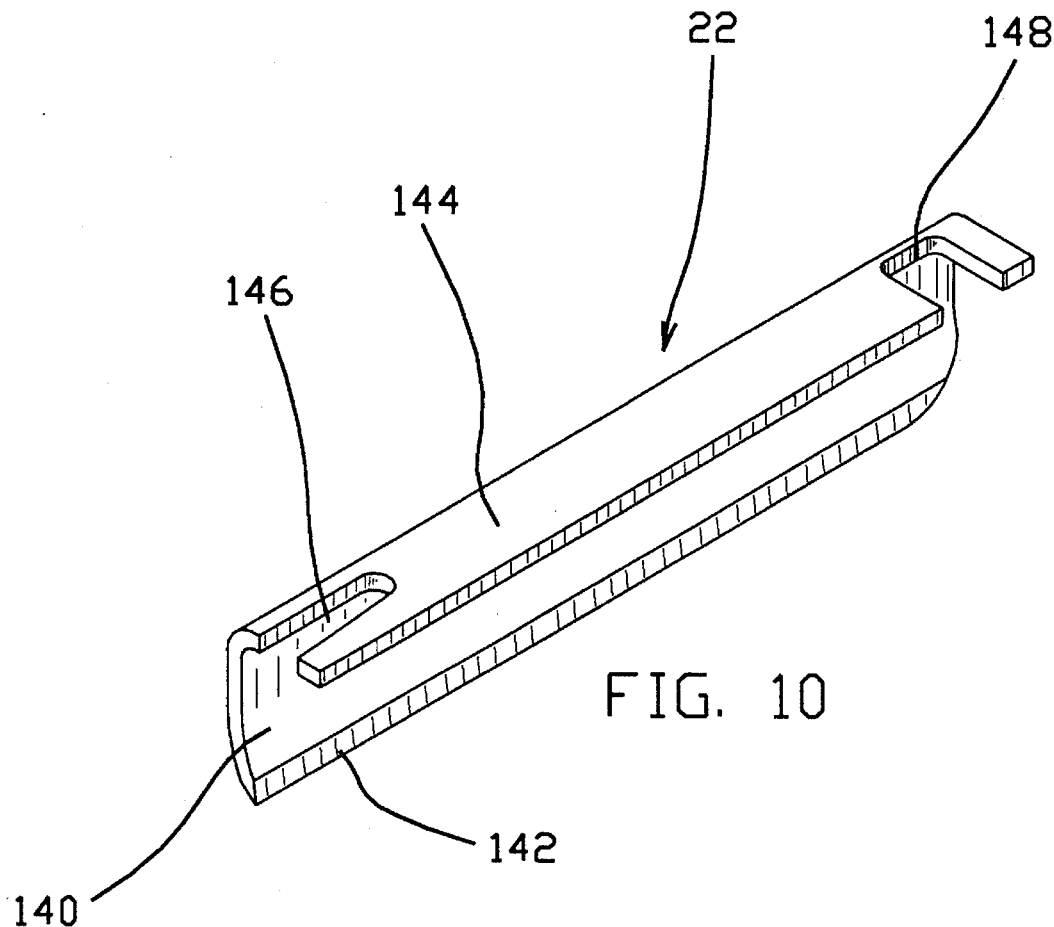
FIG. 10 is a detailed perspective view of the blade.

As shown in FIG. 10, blade 22 is an elongated and inverted "L" shaped member having a lower leg 140 with a cutting edge 142, and an upper leg 144. Notch 146 is located at the distal end of upper leg 144. Notch 148 extends through upper leg 144 at the proximal end of blade 22.

As shown in FIG. 4, upper jaw 18 includes a blade-receiving slot 101 which extends longitudinally along the length of grasping member 100. Keeper pin 103 extends through the center of slot 101 near the distal end of grasping member 100, and is rigidly mounted to the grasping member.

Figure 11:
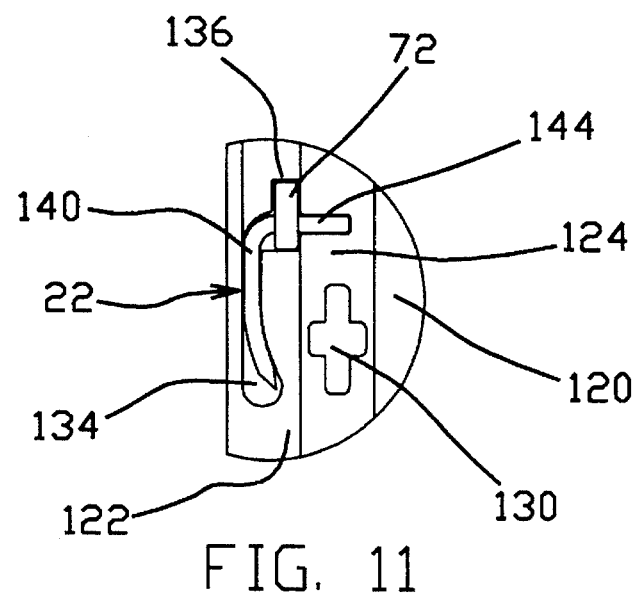
FIG. 11 is an end view of the jaw holder shown in FIG. 6, without the jaws and with the blade in the retracted position.

Blade actuator bar 72 (FIGS. 9, 11 and 12) is slidably mounted within slot 136 and includes a hook 150 on its distal end. Hook 150 is sized to engage notch 148 of blade 22. When actuator bar 72 is retracted by actuation of knobs 30, blade 22 is positioned in a retracted position within guide slot 134 of jaw holder 90. To extend blade 22 to its cutting position on upper jaw 18, the upper jaw and lower jaw 20 must be closed so blade-receiving slot 101 is aligned with blade guide slot 134. Actuator bar 72 is then moved toward jaws 18 and 20 by actuation of knobs 30. This forward motion of actuator bar 72 slides blade 22 out of guide slot 134 and into its cutting position with upper leg 144 engaged with slot 101 and notch 146 engaged with keeper pin 103. With blade 22 in this cutting position, the actuation of trigger 28 to open and close jaws 18 and 20 causes cutting edge 142 of the blade to cooperate with the edge of lower jaw 20 in a scissors-like cutting motion. Notch 148 in the blade 22 is sized large enough to accommodate the pivotal motion of the blade with upper jaw 18 while actuator bar 72 remains in a stationary position. Engagement of notch 146 with keeper pin 103 keeps blade 22 fixed within slot 101 of jaw 18 when lateral loads are imparted to the blade during the cutting function. As shown in FIG. 5, the edge of jaw 20 engaged by cutting edge 142 of blade 22 includes a taper 109 which facilitates the cutting operation with the blade. When jaws 18 and 20 are closed, knobs 30 can be actuated to slide actuator bar 72 toward handle assembly 12, thereby moving blade 22 to its retracted position within slot 134.

Multifunctional minimally invasive surgical instrument 10 offers considerable advantages. Grasping, manipulating, retracting, cutting, cauterizing, irrigating, suction and electrosurgery functions can all be provided at a minimally invasive operative site without the need to withdraw and insert different instruments. The instrument is symmetrical, so it can be used by either left-handed or right-handed surgeons. The ergonomic design of the instrument enables the surgeon to access the entire tool set with one hand while at the same time firmly grasping the instrument. The tool set can also be rotated and articulated to access surgical sites while the handle remains in an ergonomic position for the surgeon. The instrument can be disassembled and effectively sterilized. The instrument also offers a high degree of reliability during surgery.

Although the present invention has been described with reference preferred embodiments, those skilled in the art will recognize that changes may be made in form and detail without departing from the spirit and scope of the invention.

What is claimed is:

1. A multifunctional minimally invasive surgical instrument, including:

a handle assembly, including:
a handgrip;
a jaw actuator movably mounted to the handgrip; and
a blade actuator movably mounted to the handgrip;

a support tube extending from the handle assembly and having a distal end;

first and second jaws mounted to the distal end of the support tube for pivotal grasping cooperation with respect to one another, the first jaw including a blade-receiving structure;

a blade configured for movement between a retracted position within the distal end of the support tube, and a cutting position engaged with the blade-receiving structure of the first jaw and in cutting cooperation with the second jaw;

a blade linkage extending through the support tube and coupling the blade actuator to the blade, for causing the blade to move between the retracted and cutting positions in response to actuation of the blade actuator; and a jaw linkage extending through the support tube and coupling the jaw actuator to at least one of the first and second jaws, for causing the jaws to open and close in grasping cooperation in response to actuation of the jaw actuator when the blade is in the retracted position, and for causing the blade to move in cutting cooperation with the second jaw when the blade is in the cutting position.

2. The multifunctional surgical instrument of claim 1 and further including:

a fluid tip within the tube and configured for movement between a retracted position between the jaws and the handle assembly and an extended position beyond the jaws;

a tip actuator movably mounted to the handle assembly;

a tip linkage coupling the fluid tip to the tip actuator, for causing the fluid tip to move between the extended and retracted positions in response to actuation of the tip actuator;

at least one source tube extending from the fluid tip through the support tube, for coupling the fluid tip to at least one fluid source; and a fluid control member mounted to the handle assembly for controlling fluid flow through each fluid source tube.

3. The multifunctional surgical instrument of claim 2 wherein:

the fluid tip includes a suction/irrigation tip;

the instrument includes suction and irrigation source tubes for coupling the suction/irrigation tip to suction and irrigation sources, respectively; and the instrument includes suction and irrigation control members mounted to the handle assembly for controlling suction and irrigation fluid flow through the suction and irrigation source tubes, respectively.

4. The multifunctional surgical instrument of claim 2 wherein each fluid control member includes a finger-actuated pinch valve mounted to the handgrip for releasably pinching the associated source tube.

5. The multifunctional surgical instrument of claim 2 wherein the tip actuator includes a thumb-actuated switch extending from the handle assembly.

6. The multifunctional surgical instrument of claim 2 and further including a rotating mount for mounting the first and second jaws, the blade and the fluid tip for rotation with respect to the handle assembly.

7. The multifunctional surgical instrument of claim 6 wherein the rotating mount includes:

means for rotatably mounting the support tube to the handle assembly; and a knob mounted to the support tube for rotating the support tube with respect to the handle assembly.

8. The multifunctional surgical instrument of claim 1 wherein:

at least one of the jaws includes an electrically conductive member; and the instrument further includes an electrical conductor extending from the electrically conductive jaw member through the support tube, for coupling electricity to the electrically conductive jaw member.

9. The multifunctional surgical instrument of claim 1 wherein:

the first and second jaws include electrically conductive members; and the instrument further includes first and second electrical conductors for extending from the electrically conductive members of the first and second jaws through the support tube, for independently coupling electricity to the electrically conductive members of the first and second jaws, respectively.

10. The multifunctional surgical instrument of claim 1 and further including a rotating mount for mounting the first and second jaws and blade for rotation with respect to the handle assembly.

11. The multifunctional surgical instrument of claim 10 wherein the rotating mount includes:

means for rotatably mounting the support tube to the handle assembly; and a knob mounted to the support tube for rotating the support tube with respect to the handle assembly.

12. The multifunctional surgical instrument of claim 1 and further including an articulating mount for mounting the first and second jaws and blade for articulation with respect to the handle assembly.

13. The multifunctional surgical instrument of claim 12 wherein:

the articulating mount includes an articulating joint for articulating the distal end of the support tube;

the handle assembly further includes an articulation actuator movably mounted with respect to the handgrip; and the instrument further includes an articulation linkage coupling the articulation actuator to the distal end of the support tube, for causing the distal end of the support tube to articulate in response to actuation of the articulation actuator.

14. The multifunctional surgical instrument of claim 1 and further including:

a jaw holder mounted to the distal end of the support tube; and a pivot mount for pivotally mounting the first and second jaws to the jaw holder.

15. The multifunctional surgical instrument of claim 14 wherein:

the first and second jaws include elongated slots between the pivot mount and the handle assembly; and the jaw linkage includes pins extending through the elongated slots, for sliding motion within the slots and causing the jaws to open and close in response to actuation of the jaw actuator.

16. The multifunctional surgical instrument of claim 14 wherein the jaw actuator includes a trigger mounted to the handgrip.

17. The multifunctional surgical instrument of claim 16 wherein the jaw actuator includes a thumb-actuated trigger mounted to the handgrip.

18. The multifunctional surgical instrument of claim 1 wherein the jaw actuator includes a thumb-actuated trigger mounted to the handgrip.

19. The multifunctional surgical instrument of claim 1 and further including a guide slot in the distal end of the support tube for enclosing the blade when the blade is in the retracted position, and for guiding the blade onto the first jaw when the jaws are closed and the blade is being moved to the cutting position.

20. The multifunctional surgical instrument of claim 1 wherein:

the blade-receiving structure of the first jaw includes a slot; and the blade includes a leg slidably engaged in the slot of the first jaw.

21. The multifunctional surgical instrument of claim 20 wherein:

the blade-receiving structure of the first jaw includes a keeper pin extending between opposite sides of the slot; and the blade further includes a notch in the distal end of the leg for engaging the keeper pin in the first jaw when the blade is in the cutting position.

22. The multifunctional surgical instrument of claim 20 wherein:

the leg of the blade includes an aperture; and the blade linkage includes a hook for engaging the aperture in the blade.

23. The multifunctional surgical instrument of claim 1 wherein the blade actuator includes a finger-actuated knob extending from the handle assembly.

24. A multifunctional minimally invasive surgical instrument, including a handle assembly, including:
a hand grip;
a jaw actuator movably mounted to the hand grip;
a blade actuator movably mounted to the hand grip;
a suction/irrigation tip actuator movably mounted to the hand grip; and
an articulation actuator movably mounted to the hand grip;

a support tube extending from the handle assembly and having a distal end;

first and second jaws mounted to the distal end of the support tube for pivotal grasping cooperation with respect to one another, the first jaw including a blade-receiving structure;

a blade configured for movement between a retracted position within the distal end of the support tube, and a cutting position engaged with the blade-receiving structure of the first jaw and in cutting cooperation with the second jaw;

a blade linkage extending through the support tube and coupling the blade actuator to the blade, for causing the blade to move between the retracted and cutting positions in response to actuation of the blade actuator;

a jaw linkage extending through the support tube and coupling the jaw actuator to at least one of the first and second jaws, for causing the jaws to open and close in grasping cooperation in response to actuation of the jaw actuator when the blade is in the retracted position, and for causing the blade to move in cutting cooperation with the second jaw when the blade is in the cutting position;

an articulation linkage for causing the distal end of the support tube to articulate in response to actuation of the articulation actuator;

a suction/irrigation tip linkage coupling the suction/irrigation tip to the suction/irrigation tip actuator, for causing the suction/irrigation tip to move between the extended and retracted positions in response to actuation of the suction/irrigation tip actuator;

at least one source tube extending from the suction/irrigation tip through the support tube, for coupling the suction/irrigation tip to suction and irrigation sources;

a rotatable mount for rotatably mounting the support tube to the handle assembly; and a knob for rotating the support tube with respect to the handle assembly.

* * * * *